US012778557B2

(12) United States Patent
Sowards et al.

(10) Patent No.: US 12,778,557 B2
(45) Date of Patent: Nov. 3, 2026

(54) MEDICAL DEVICE SYSTEM HAVING BLOOD VESSEL CORRELATION TOOLS

(71) Applicant: Bard Access Systems, Inc., Salt Lake City, UT (US)

(72) Inventors: Steffan Sowards, Salt Lake City, UT (US); William Robert McLaughlin, Bountiful, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/722,151

(22) Filed: Apr. 15, 2022

(65) Prior Publication Data

US 2022/0330922 A1 Oct. 20, 2022

Related U.S. Application Data

(60) Provisional application No. 63/175,484, filed on Apr. 15, 2021.

(51) Int. Cl.
*A61B 8/00* (2006.01)
*A61B 8/08* (2006.01)
(Continued)

(52) U.S. Cl.
CPC .......... *A61B 8/5261* (2013.01); *A61B 8/0891* (2013.01); *A61B 8/463* (2013.01); *G16H 30/40* (2018.01); *G16H 40/63* (2018.01)

(58) Field of Classification Search
CPC ..... A61B 8/5261; A61B 8/4472; A61B 8/463; A61B 8/0891; A61B 8/461; A61B 8/46;
(Continued)

(56) References Cited

U.S. PATENT DOCUMENTS 3,697,917 A 10/1972 Orth et al.
5,148,809 A 9/1992 Biegeleisen-Knight et al.
(Continued)

FOREIGN PATENT DOCUMENTS

CN 102871645 A 1/2013
CN 105107067 B 5/2018
(Continued)

OTHER PUBLICATIONS

PCT/US2022/048716 filed Nov. 2, 2022 International Search Report and Written Opinion dated Feb. 24, 2023.
(Continued)

*Primary Examiner* — Anh Tuan T Nguyen
*Assistant Examiner* — Dean N Edun
(74) *Attorney, Agent, or Firm* — Rutan & Tucker LLP

(57) ABSTRACT

Disclosed herein is a medical device system configured to detect one or more blood vessels within a target area. The medical device system includes an ultrasound probe configured to detect one or more blood vessels, the ultrasound probe in communication with a console. The medical device system further includes one or more blood vessel correlation tools configured to generate a local output detectable by a user. The one or more blood vessel correlation tools are coupled to the ultrasound probe and in communication with a console. The one or more blood vessel correlation tools are selected from the group consisting of a light array, one or more visible light projectors, a haptic feedback system, and an auditory device.

24 Claims, 6 Drawing Sheets

(51) Int. Cl.
*G16H 30/40* (2018.01)
*G16H 40/63* (2018.01)

(58) Field of Classification Search
CPC ......... A61B 8/4444; A61B 8/54; A61B 8/085; A61B 8/5223; A61B 8/0841; A61B 8/469; A61B 8/4254; A61B 8/4427; A61B 5/489; A61B 2017/3413; A61B 2090/378; A61B 17/3403; A61B 5/742; A61B 2034/107; A61B 5/02007; G16H 40/63; G16H 30/40; G06T 2207/10132; G06T 7/0012; G06T 2207/30101; G06T 7/12; G06T 7/62
See application file for complete search history.

(56) References Cited

U.S. PATENT DOCUMENTS 5,181,513 A 1/1993 Touboul et al.
5,325,293 A 6/1994 Dorne
5,349,865 A 9/1994 Kavli et al.
5,441,052 A 8/1995 Miyajima
5,549,554 A 8/1996 Miraki
5,573,529 A 11/1996 Haak et al.
5,758,650 A 6/1998 Miller et al.
5,775,322 A 7/1998 Silverstein et al.
5,879,297 A 3/1999 Haynor et al.
5,897,503 A 4/1999 Lyon et al.
5,908,387 A 6/1999 LeFree et al.
5,967,984 A 10/1999 Chu et al.
5,970,119 A 10/1999 Hofmann
6,004,270 A 12/1999 Urbano et al.
6,019,724 A 2/2000 Gronningsaeter et al.
6,068,599 A 5/2000 Saito et al.
6,074,367 A 6/2000 Hubbell
6,129,668 A 10/2000 Haynor et al.
6,132,379 A 10/2000 Patacsil et al.
6,216,028 B1 4/2001 Haynor et al.
6,233,476 B1 5/2001 Strommer et al.
6,245,018 B1 6/2001 Lee
6,263,230 B1 7/2001 Haynor et al.
6,375,615 B1 4/2002 Flaherty et al.
6,436,043 B2 8/2002 Bonnefous
6,498,942 B1 12/2002 Esenaliev et al.
6,503,205 B2 1/2003 Manor et al.
6,508,769 B2 1/2003 Bonnefous
6,511,458 B2 1/2003 Milo et al.
6,524,249 B2 2/2003 Moehring et al.
6,543,642 B1 4/2003 Milliorn
6,554,771 B1 4/2003 Buil et al.
6,592,520 B1 7/2003 Peszynski et al.
6,592,565 B2 7/2003 Twardowski
6,601,705 B2 8/2003 Molina et al.
6,612,992 B1 9/2003 Hossack et al.
6,613,002 B1 9/2003 Clark et al.
6,623,431 B1 9/2003 Sakuma et al.
6,641,538 B2 11/2003 Nakaya et al.
6,647,135 B2 11/2003 Bonnefous
6,687,386 B1 2/2004 Ito et al.
6,733,458 B1 5/2004 Steins et al.
6,749,569 B1 6/2004 Pellegretti
6,754,608 B2 6/2004 Svanerudh et al.
6,755,789 B2 6/2004 Stringer et al.
6,840,379 B2 1/2005 Franks-Farah et al.
6,857,196 B2 2/2005 Dalrymple
6,979,294 B1 12/2005 Selzer et al.
7,074,187 B2 7/2006 Selzer et al.
7,244,234 B2 7/2007 Ridley et al.
7,359,554 B2 4/2008 Klingensmith et al.
7,534,209 B2 5/2009 Abend et al.
7,599,730 B2 10/2009 Hunter et al.
7,637,870 B2 12/2009 Flaherty et al.
7,681,579 B2 3/2010 Schwartz
7,691,061 B2 4/2010 Hirota
7,699,779 B2 4/2010 Sasaki et al.
7,720,520 B2 5/2010 Willis
7,727,153 B2 6/2010 Fritz et al.
7,734,326 B2 6/2010 Pedain et al.
7,831,449 B2 11/2010 Mng et al.
7,905,837 B2 3/2011 Suzuki
7,925,327 B2 4/2011 Weese
7,927,278 B2 4/2011 Selzer et al.
8,014,848 B2 9/2011 Birkenbach et al.
8,038,619 B2 10/2011 Steinbacher
8,060,181 B2 11/2011 Rodriguez Ponce et al.
8,075,488 B2 12/2011 Burton
8,090,427 B2 1/2012 Eck et al.
8,105,239 B2 1/2012 Specht
8,172,754 B2 5/2012 Watanabe et al.
8,175,368 B2 5/2012 Sathyanarayana
8,200,313 B1 6/2012 Rambod et al.
8,211,023 B2 7/2012 Swan et al.
8,228,347 B2 7/2012 Beasley et al.
8,298,147 B2 10/2012 Huennekens et al.
8,303,505 B2 11/2012 Webler et al.
8,323,202 B2 12/2012 Roschak et al.
8,328,727 B2 12/2012 Miele et al.
8,336,536 B1 12/2012 Wood-Putnam et al.
8,388,541 B2 3/2013 Messerly et al.
8,409,103 B2 4/2013 Grunwald et al.
8,449,465 B2 5/2013 Nair et al.
8,553,954 B2 10/2013 Saikia
8,556,815 B2 10/2013 Pelissier et al.
8,585,600 B2 11/2013 Liu et al.
8,622,913 B2 1/2014 Dentinger et al.
8,706,457 B2 4/2014 Hart et al.
8,727,988 B2 5/2014 Flaherty et al.
8,734,357 B2 5/2014 Taylor
8,744,211 B2 6/2014 Owen
8,754,865 B2 6/2014 Merritt et al.
8,764,663 B2 7/2014 Smok et al.
8,781,194 B2 7/2014 Malek et al.
8,781,555 B2 7/2014 Burnside et al.
8,790,263 B2 7/2014 Randall et al.
8,849,382 B2 9/2014 Cox et al.
8,939,908 B2 1/2015 Suzuki et al.
8,961,420 B2 2/2015 Zhang
9,022,940 B2 5/2015 Meier
9,087,147 B1 7/2015 Fonte
9,138,290 B2 9/2015 Hadjicostis
9,199,082 B1 12/2015 Yared et al.
9,204,858 B2 12/2015 Pelissier et al.
9,220,477 B2 12/2015 Urabe et al.
9,295,447 B2 3/2016 Shah
9,320,493 B2 4/2016 Visveshwara
9,357,980 B2 6/2016 Toji et al.
9,364,171 B2 6/2016 Harris et al.
9,427,207 B2 8/2016 Sheldon et al.
9,445,780 B2 9/2016 Hossack et al.
9,456,766 B2 10/2016 Cox et al.
9,456,804 B2 10/2016 Tamada
9,468,413 B2 10/2016 Hall et al.
9,492,097 B2 11/2016 Wilkes et al.
9,521,961 B2 12/2016 Silverstein et al.
9,554,716 B2 1/2017 Burnside et al.
9,582,876 B2 2/2017 Specht
9,610,061 B2 4/2017 Ebbini et al.
9,636,031 B2 5/2017 Cox
9,649,037 B2 5/2017 Lowe et al.
9,649,048 B2 5/2017 Cox et al.
9,702,969 B2 7/2017 Hope Simpson et al.
9,715,757 B2 7/2017 Ng et al.
9,717,415 B2 8/2017 Cohen et al.
9,731,066 B2 8/2017 Liu et al.
9,814,433 B2 11/2017 Benishti et al.
9,814,531 B2 11/2017 Yagi et al.
9,861,337 B2 1/2018 Patwardhan et al.
9,895,138 B2 2/2018 Sasaki
9,913,605 B2 3/2018 Harris et al.
9,949,720 B2 4/2018 Southard et al.
10,043,272 B2 8/2018 Forzoni et al.
10,449,330 B2 10/2019 Newman et al.
10,524,691 B2 1/2020 Newman et al.
10,751,509 B2 8/2020 Misener

(56) References Cited

U.S. PATENT DOCUMENTS 11,564,861 B1 1/2023 Gaines
11,844,656 B2 12/2023 Urabe et al.
11,900,593 B2 2/2024 Dhatt et al.
12,082,976 B2 9/2024 Urabe et al.
2002/0038088 A1 3/2002 Imran et al.
2003/0047126 A1 3/2003 Tomaschko
2003/0106825 A1 6/2003 Molina et al.
2003/0109910 A1 6/2003 Lachenbruch et al.
2003/0120154 A1 6/2003 Sauer et al.
2003/0125629 A1* 7/2003 Ustuner ................. A61B 46/00 600/459
2003/0135115 A1 7/2003 Burdette et al.
2003/0149366 A1 8/2003 Stringer et al.
2003/0167030 A1 9/2003 Weitzel et al.
2003/0216648 A1 11/2003 Lizzi et al.
2004/0015080 A1 1/2004 Kelly et al.
2004/0055925 A1 3/2004 Franks-Farah et al.
2004/0197267 A1 10/2004 Black et al.
2005/0000975 A1 1/2005 Carco et al.
2005/0049504 A1 3/2005 Lo et al.
2005/0075597 A1 4/2005 Vournakis et al.
2005/0165299 A1 7/2005 Kressy et al.
2005/0251030 A1 11/2005 Azar et al.
2005/0267365 A1 12/2005 Sokulin et al.
2006/0004290 A1 1/2006 Smith et al.
2006/0013523 A1 1/2006 Childlers et al.
2006/0015039 A1 1/2006 Cassidy et al.
2006/0020204 A1 1/2006 Serra et al.
2006/0047617 A1 3/2006 Bacioiu et al.
2006/0079781 A1 4/2006 Germond-Rouet et al.
2006/0184029 A1 8/2006 Haim et al.
2006/0210130 A1 9/2006 Germond-Rouet et al.
2006/0241463 A1 10/2006 Shau et al.
2007/0043341 A1 2/2007 Anderson et al.
2007/0049822 A1 3/2007 Bunce et al.
2007/0073155 A1 3/2007 Park et al.
2007/0167738 A1 7/2007 Timinger et al.
2007/0199848 A1 8/2007 Ellswood et al.
2007/0239005 A1 10/2007 Ogasawara
2007/0239120 A1 10/2007 Brock et al.
2007/0249911 A1 10/2007 Simon
2007/0287886 A1 12/2007 Saadat
2008/0021322 A1 1/2008 Stone et al.
2008/0033293 A1 2/2008 Beasley et al.
2008/0033759 A1 2/2008 Finlay
2008/0051657 A1 2/2008 Rold
2008/0108930 A1 5/2008 Weitzel et al.
2008/0125651 A1 5/2008 Watanabe et al.
2008/0146915 A1 6/2008 McMorrow
2008/0177186 A1 7/2008 Slater et al.
2008/0221425 A1 9/2008 Olson et al.
2008/0269605 A1 10/2008 Nakaya
2008/0294037 A1 11/2008 Richter
2008/0300491 A1 12/2008 Bonde et al.
2009/0012399 A1 1/2009 Sunagawa et al.
2009/0012401 A1 1/2009 Steinbacher
2009/0074280 A1 3/2009 Lu et al.
2009/0105594 A1* 4/2009 Reynolds ................. A61B 8/06 600/454
2009/0118612 A1 5/2009 Grunwald et al.
2009/0124903 A1 5/2009 Osaka
2009/0137887 A1 5/2009 Shariati et al.
2009/0137907 A1 5/2009 Takimoto et al.
2009/0143672 A1 6/2009 Harms et al.
2009/0143684 A1 6/2009 Cermak et al.
2009/0156926 A1 6/2009 Messerly et al.
2009/0171205 A1 7/2009 Kharin et al.
2009/0281413 A1 11/2009 Boyden et al.
2009/0306509 A1 12/2009 Pedersen et al.
2010/0010348 A1 1/2010 Halmann
2010/0168576 A1 7/2010 Poland et al.
2010/0211026 A2 8/2010 Sheetz et al.
2010/0249598 A1 9/2010 Smith et al.
2010/0286515 A1 11/2010 Gravenstein et al.
2010/0298705 A1 11/2010 Pelissier et al.
2010/0312121 A1 12/2010 Guan
2010/0324423 A1 12/2010 El-Aklouk et al.
2011/0002518 A1 1/2011 Ziv-Ari et al.
2011/0026796 A1 2/2011 Hyun et al.
2011/0071404 A1 3/2011 Schmitt et al.
2011/0074244 A1 3/2011 Osawa
2011/0087107 A1 4/2011 Lindekugel et al.
2011/0137173 A1 6/2011 Lowe et al.
2011/0166451 A1 7/2011 Blaivas et al.
2011/0282188 A1 11/2011 Burnside et al.
2011/0295108 A1 12/2011 Cox et al.
2011/0313293 A1 12/2011 Lindekugel et al.
2012/0136242 A1 5/2012 Qi et al.
2012/0136256 A1* 5/2012 Nozaki .................. A61B 8/469 600/459
2012/0143029 A1 6/2012 Silverstein et al.
2012/0165679 A1 6/2012 Orome et al.
2012/0179038 A1 7/2012 Meurer et al.
2012/0179042 A1 7/2012 Fukumoto et al.
2012/0179044 A1 7/2012 Chiang et al.
2012/0197132 A1 8/2012 O'Connor
2012/0220865 A1 8/2012 Brown et al.
2012/0277576 A1 11/2012 Lui
2013/0041250 A1 2/2013 Pelissier et al.
2013/0102889 A1 4/2013 Southard et al.
2013/0131499 A1 5/2013 Chan et al.
2013/0131502 A1 5/2013 Blaivas et al.
2013/0144166 A1 6/2013 Specht et al.
2013/0150724 A1 6/2013 Blaivas et al.
2013/0188832 A1 7/2013 Ma et al.
2013/0197367 A1* 8/2013 Smok ..................... A61B 8/488 600/454
2013/0218024 A1 8/2013 Boctor et al.
2013/0323700 A1 12/2013 Samosky et al.
2013/0338503 A1 12/2013 Cohen et al.
2013/0338508 A1 12/2013 Nakamura et al.
2013/0345566 A1 12/2013 Weitzel et al.
2014/0005530 A1 1/2014 Liu et al.
2014/0031694 A1 1/2014 Solek
2014/0066779 A1 3/2014 Nakanishi
2014/0073976 A1 3/2014 Fonte et al.
2014/0100440 A1 4/2014 Cheline et al.
2014/0114194 A1 4/2014 Kanayama et al.
2014/0170620 A1 6/2014 Savitsky et al.
2014/0180098 A1 6/2014 Flaherty et al.
2014/0180116 A1 6/2014 Lindekugel et al.
2014/0188133 A1 7/2014 Misener
2014/0188440 A1 7/2014 Donhowe et al.
2014/0276048 A1 9/2014 Kiley et al.
2014/0276059 A1 9/2014 Sheehan
2014/0276069 A1 9/2014 Amble et al.
2014/0276081 A1 9/2014 Tegels
2014/0276085 A1 9/2014 Miller
2014/0276690 A1 9/2014 Grace
2014/0296694 A1 10/2014 Jaworski
2014/0343431 A1 11/2014 Vajinepalli et al.
2014/0357994 A1 12/2014 Jin et al.
2015/0005738 A1 1/2015 Blacker
2015/0011887 A1* 1/2015 Ahn ....................... A61B 8/085 600/454
2015/0011900 A1 1/2015 Lu et al.
2015/0065916 A1 3/2015 Maguire et al.
2015/0073279 A1 3/2015 Cai et al.
2015/0080740 A1* 3/2015 Hao ....................... A61B 90/11 600/476
2015/0112200 A1 4/2015 Oberg et al.
2015/0141821 A1 5/2015 Yoshikawa et al.
2015/0190111 A1 7/2015 Fry
2015/0209003 A1 7/2015 Halmann et al.
2015/0209113 A1 7/2015 Burkholz et al.
2015/0209510 A1 7/2015 Burkholz et al.
2015/0209526 A1 7/2015 Matsubara et al.
2015/0245820 A1 9/2015 Tamada
2015/0257735 A1 9/2015 Ball et al.
2015/0272448 A1 10/2015 Fonte et al.
2015/0282890 A1 10/2015 Cohen et al.
2015/0294497 A1 10/2015 Ng et al.
2015/0297097 A1 10/2015 Matsubara et al.
2015/0342572 A1 12/2015 Tahmasebi Maraghoosh et al.

(56) References Cited

U.S. PATENT DOCUMENTS

2015/0359520 A1 12/2015 Shan et al.
2015/0359991 A1 12/2015 Dunbar et al.
2016/0000367 A1 1/2016 Lyon
2016/0000399 A1 1/2016 Halmann et al.
2016/0026894 A1 1/2016 Nagase
2016/0029995 A1 2/2016 Navratil et al.
2016/0038119 A1 2/2016 Desjardins
2016/0081674 A1 3/2016 Bagwan et al.
2016/0113517 A1 4/2016 Lee et al.
2016/0113699 A1 4/2016 Sverdlik et al.
2016/0120607 A1 5/2016 Sorotzkin et al.
2016/0125639 A1 5/2016 Park et al.
2016/0157831 A1 6/2016 Kang et al.
2016/0166232 A1 6/2016 Merritt
2016/0202053 A1 7/2016 Walker et al.
2016/0211045 A1 7/2016 Jeon et al.
2016/0213398 A1 7/2016 Liu
2016/0220124 A1 8/2016 Grady et al.
2016/0259992 A1 9/2016 Knodt et al.
2016/0278869 A1 9/2016 Grunwald
2016/0287214 A1 10/2016 Ralovich et al.
2016/0296208 A1 10/2016 Sethuraman et al.
2016/0374644 A1 12/2016 Mauldin, Jr. et al.
2017/0014105 A1 1/2017 Chono
2017/0020561 A1 1/2017 Cox et al.
2017/0079548 A1 3/2017 Silverstein et al.
2017/0086785 A1 3/2017 Bjaerum
2017/0090571 A1* 3/2017 Bjaerum .............. A61B 8/4254
2017/0103534 A1 4/2017 Park et al.
2017/0143312 A1 5/2017 Hedlund et al.
2017/0157339 A1 6/2017 Li et al.
2017/0164923 A1 6/2017 Matsumoto
2017/0172666 A1 6/2017 Govari et al.
2017/0215842 A1 8/2017 Ryu et al.
2017/0231553 A1* 8/2017 Igarashi ................. A61B 18/00 600/479
2017/0252004 A1 9/2017 Broad et al.
2017/0258522 A1 9/2017 Goshgarian et al.
2017/0259013 A1* 9/2017 Boyden .................. G16H 30/40
2017/0262982 A1 9/2017 Pagoulatos et al.
2017/0328751 A1 11/2017 Lemke
2017/0367678 A1 12/2017 Sirtori et al.
2018/0015256 A1 1/2018 Southard et al.
2018/0028110 A1* 2/2018 Goldman .............. A61M 5/427
2018/0116723 A1 5/2018 Hettrick et al.
2018/0125450 A1 5/2018 Blackbourne et al.
2018/0161502 A1 6/2018 Nanan et al.
2018/0199914 A1 7/2018 Ramachandran et al.
2018/0214119 A1 8/2018 Mehrmohammadi et al.
2018/0228465 A1* 8/2018 Southard .............. A61B 8/4427
2018/0235649 A1 8/2018 Elkadi
2018/0235709 A1 8/2018 Donhowe et al.
2018/0289927 A1 10/2018 Messerly
2018/0296185 A1 10/2018 Cox et al.
2018/0310955 A1 11/2018 Lindekugel et al.
2018/0333135 A1 11/2018 Kim et al.
2018/0344293 A1 12/2018 Raju et al.
2019/0029636 A1 1/2019 Lee et al.
2019/0060001 A1 2/2019 Kohli et al.
2019/0060014 A1 2/2019 Hazelton et al.
2019/0090855 A1 3/2019 Kobayashi et al.
2019/0125210 A1 5/2019 Govari et al.
2019/0200951 A1 7/2019 Meier
2019/0239848 A1 8/2019 Bedi et al.
2019/0239850 A1 8/2019 Dalvin et al.
2019/0307419 A1 10/2019 Durfee
2019/0307515 A1 10/2019 Naito et al.
2019/0307516 A1 10/2019 Schotzko et al.
2019/0365347 A1* 12/2019 Abe ..................... A61B 5/0095
2019/0365348 A1 12/2019 Toume et al.
2019/0365354 A1 12/2019 Du
2019/0380676 A1 12/2019 Swan et al.
2020/0027210 A1 1/2020 Haemel et al.
2020/0069929 A1 3/2020 Mason et al.
2020/0085381 A1 3/2020 Weine et al.
2020/0107596 A1 4/2020 Caruso et al.
2020/0113540 A1 4/2020 Gijsbers et al.
2020/0163654 A1 5/2020 Satir et al.
2020/0200900 A1 6/2020 Asami et al.
2020/0229795 A1 7/2020 Tadross et al.
2020/0230391 A1 7/2020 Burkholz et al.
2020/0237403 A1 7/2020 Southard et al.
2020/0238403 A1 7/2020 Ahn et al.
2020/0281563 A1 9/2020 Muller et al.
2020/0359990 A1 11/2020 Poland et al.
2020/0390416 A1 12/2020 Swan et al.
2021/0045716 A1 2/2021 Shiran et al.
2021/0059639 A1 3/2021 Howell
2021/0077058 A1 3/2021 Mashood et al.
2021/0093383 A1 4/2021 Wang et al.
2021/0137492 A1* 5/2021 Imai ....................... A61B 8/488
2021/0146167 A1 5/2021 Barthe et al.
2021/0161510 A1 6/2021 Sasaki et al.
2021/0186467 A1 6/2021 Urabe et al.
2021/0212658 A1* 7/2021 McGrath .............. A61B 8/4494
2021/0212668 A1 7/2021 Li et al.
2021/0267569 A1 9/2021 Yamamoto
2021/0267570 A1 9/2021 Ulman et al.
2021/0295048 A1 9/2021 Buras et al.
2021/0315538 A1 10/2021 Brandl et al.
2021/0373602 A1 12/2021 Min
2021/0378627 A1 12/2021 Yarmush et al.
2022/0019313 A1 1/2022 He et al.
2022/0022969 A1 1/2022 Misener
2022/0039777 A1 2/2022 Durfee
2022/0039829 A1* 2/2022 Zijlstra .................. A61B 8/462
2022/0071593 A1 3/2022 Tran
2022/0096053 A1 3/2022 Sethuraman et al.
2022/0096797 A1 3/2022 Prince
2022/0101980 A1 3/2022 Rothenberg et al.
2022/0104791 A1 4/2022 Matsumoto
2022/0104886 A1 4/2022 Blanchard et al.
2022/0117582 A1 4/2022 McLaughlin et al.
2022/0160434 A1 5/2022 Messerly et al.
2022/0168050 A1 6/2022 Sowards et al.
2022/0172354 A1 6/2022 Misener et al.
2022/0225963 A1 7/2022 Sutton et al.
2022/0233346 A1 7/2022 McElya
2022/0296303 A1 9/2022 McLeod et al.
2022/0304652 A1 9/2022 Peterson et al.
2022/0334251 A1 10/2022 Sowards et al.
2022/0338833 A1 10/2022 Dhatt et al.
2022/0361840 A1 11/2022 Matsumoto et al.
2022/0406460 A1 12/2022 Golan et al.
2023/0044620 A1 2/2023 Shochat et al.
2023/0048327 A1 2/2023 Lampe et al.
2023/0107629 A1 4/2023 Sowards et al.
2023/0113291 A1* 4/2023 de Wild ............... A61B 8/0841 600/443
2023/0132148 A1 4/2023 Sowards et al.
2023/0135562 A1 5/2023 Misener et al.
2023/0135757 A1 5/2023 Bauer et al.
2023/0138970 A1 5/2023 Sowards et al.
2023/0148872 A1 5/2023 Sowards et al.
2023/0201539 A1 6/2023 Howell
2023/0277153 A1 9/2023 Sowards et al.
2023/0277154 A1 9/2023 Sowards et al.
2023/0293143 A1 9/2023 Sowards et al.
2023/0298757 A1 9/2023 Golan et al.
2023/0338010 A1 10/2023 Sturm
2023/0371928 A1 11/2023 Rajguru et al.
2023/0381472 A1 11/2023 Chisena et al.
2023/0397900 A1 12/2023 Prince
2024/0065673 A1 2/2024 Sowards et al.
2024/0197403 A1 6/2024 Mino et al.
2024/0307024 A1 9/2024 Sowards et al.
2025/0017559 A1 1/2025 Denny et al.
2025/0057501 A1 2/2025 Prince
2025/0104238 A1 3/2025 Misener et al.
2025/0177060 A1 6/2025 Messerly et al.
2025/0186026 A1 6/2025 Tran
2025/0251511 A1 8/2025 Sowards et al.

(56) References Cited

U.S. PATENT DOCUMENTS

| | | | |
|---|---|---|---|
| 2025/0352167 | A1 | 11/2025 | Sowards et al. |
| 2026/0123906 | A1 | 5/2026 | Sowards et al. |

FOREIGN PATENT DOCUMENTS

| | | | |
|---|---|---|---|
| EP | 0933063 | A1 | 8/1999 |
| EP | 1504713 | A1 | 2/2005 |
| EP | 1591074 | B1 | 5/2008 |
| EP | 2823766 | A1 | 1/2015 |
| EP | 3181083 | A1 | 6/2017 |
| EP | 3870059 | | 9/2021 |
| JP | 2000271136 | A | 10/2000 |
| JP | 2007222291 | A | 9/2007 |
| JP | 2014150928 | A | 8/2014 |
| JP | 2018175547 | A | 11/2018 |
| KR | 20180070878 | A | 6/2018 |
| KR | 102176196 | B1 | 11/2020 |
| WO | 2004082749 | A2 | 9/2004 |
| WO | 2007115174 | A2 | 10/2007 |
| WO | 2010029521 | A2 | 3/2010 |
| WO | 2010076808 | A1 | 7/2010 |
| WO | 2013059714 | A1 | 4/2013 |
| WO | 2014/115150 | A1 | 7/2014 |
| WO | 2015/017270 | A1 | 2/2015 |
| WO | 2016/081023 | A1 | 5/2016 |
| WO | 2017096487 | A1 | 6/2017 |
| WO | 2017214428 | A1 | 12/2017 |
| WO | 2018/026878 | A1 | 2/2018 |
| WO | 2018134726 | A1 | 7/2018 |
| WO | 2018138343 | A1 | 8/2018 |
| WO | 2019/232451 | A1 | 12/2019 |
| WO | 2020/002620 | A1 | 1/2020 |
| WO | 2020/016018 | A1 | 1/2020 |
| WO | 2019/232454 | A9 | 2/2020 |
| WO | 2020/044769 | A1 | 3/2020 |
| WO | 2020067897 | A1 | 4/2020 |
| WO | 2020083660 | A1 | 4/2020 |
| WO | 2020/186198 | A1 | 9/2020 |
| WO | 2021123905 | A2 | 6/2021 |
| WO | 2021198226 | A1 | 10/2021 |
| WO | 2022/072727 | A2 | 4/2022 |
| WO | 2022/081904 | A1 | 4/2022 |
| WO | 2022069208 | A1 | 4/2022 |
| WO | 2022/119853 | A1 | 6/2022 |
| WO | 2022115479 | A1 | 6/2022 |
| WO | 2022119856 | A1 | 6/2022 |
| WO | 2022/221703 | A1 | 10/2022 |
| WO | 2022/221714 | A1 | 10/2022 |
| WO | 2023059512 | A1 | 4/2023 |
| WO | 2023076268 | A1 | 5/2023 |
| WO | 2023081220 | A1 | 5/2023 |
| WO | 2023081223 | A1 | 5/2023 |
| WO | 2023091424 | A1 | 5/2023 |
| WO | 2023167866 | A1 | 9/2023 |
| WO | 2023177718 | A1 | 9/2023 |
| WO | 2024044277 | A1 | 2/2024 |
| WO | 2024180503 | A1 | 9/2024 |
| WO | 2025015198 | A1 | 1/2025 |

OTHER PUBLICATIONS

PCT/US2022/048722 filed Nov. 2, 2022 International Search Report and Written Opinion dated Feb. 24, 2023.

PCT/US2022047727 filed Oct. 25, 2022 International Search Report and Written Opinion dated Jan. 25, 2023.

U.S. Appl. No. 17/020,476, filed Sep. 14, 2020 Final Office Action dated Jan. 5, 2023.

U.S. Appl. No. 17/020,476, filed Sep. 14, 2020 Non-Final Office Action dated Sep. 23, 2022.

U.S. Appl. No. 17/471,015, filed Sep. 9, 2021 Non-Final Office Action dated Mar. 30, 2023.

U.S. Appl. No. 17/534,099, filed Nov. 23, 2021 Non-Final Office Action dated Mar. 31, 2023.

U.S. Appl. No. 17/538,911, filed Nov. 30, 2021 Non-Final Office Action dated Mar. 2, 2023.

PCT/US2022/025082 filed Apr. 15, 2022 International Search Report and Written Opinion dated Jul. 11, 2022.

PCT/US2022/025097 filed Apr. 15, 2022 International Search Report and Written Opinion dated Jul. 8, 2022.

U.S. Appl. No. 17/020,476, filed Sep. 14, 2020 Advisory Action dated Aug. 19, 2022.

U.S. Appl. No. 17/471,015, filed Sep. 9, 2021 Non-Final Office Action dated Aug. 16, 2022.

PCT/US2022/049983 filed Nov. 15, 2022 International Search Report and Written Opinion dated Mar. 29, 2023.

PCT/US2023/014143 filed Feb. 28, 2023 International Search Report and Written Opinion dated Jun. 12, 2023.

PCT/US2023/015266 filed Mar. 15, 2023 International Search Report and Written Opinion dated May 25, 2023.

Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.

U.S. Appl. No. 17/020,476, filed Sep. 14, 2020 Notice of Allowance dated Apr. 28, 2022.

U.S. Appl. No. 17/468,318, filed Sep. 7, 2021 Non-Final Office Action dated Apr. 12, 2023.

U.S. Appl. No. 17/684,180, filed Mar. 1, 2022 Restriction Requirement dated May 19, 2023.

Lu Zhenyu et al."Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

Pagoulatos, N. et al. "New spatial localizer based on fiber optics with applications in 3D ultrasound imaging" Proceeding of SPIE, vol. 3976 (Apr. 18, 2000; Apr. 18, 2000).

PCT/US2021/049294 filed Sep. 7, 2021 International Search Report and Written Opinion dated Dec. 8, 2021.

PCT/US2021/049712 filed Sep. 9, 2021 International Search Report and Written Opinion dated Dec. 14, 2021.

PCT/US2021/060622 filed Nov. 23, 2021 International Search Report and Written Opinion dated Mar. 3, 2022.

PCT/US2021/061267 filed Nov. 30, 2021 International Search Report and Written Opinion dated Mar. 9, 2022.

PCT/US2021/061276 filed Nov. 30, 2021 International Search Report and Written Opinion dated Mar. 9, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/SebastianVogtDissertation.pdf.

U.S. Appl. No. 15/650,474, filed Jul. 14, 2017 Final Office Action dated Jun. 2, 2020.

U.S. Appl. No. 15/650,474, filed Jul. 14, 2017 Non-Final Office Action dated Dec. 16, 2019.

U.S. Appl. No. 15/650,474, filed Jul. 14, 2017 Notice of Allowance dated Dec. 11, 2020.

U.S. Appl. No. 15/650,474, filed Jul. 14, 2017 Notice of Allowance dated Mar. 1, 2021.

U.S. Appl. No. 17/020,476, filed Sep. 14, 2020 Final Office Action dated Jun. 9, 2022.

U.S. Appl. No. 17/020,476, filed Sep. 14, 2020 Non-Final Office Action dated Feb. 9, 2022.

William F Garrett et al: "Real-time incremental visualization of dynamic ultrasound vols. using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

EP 20866520.8 filed Apr. 5, 2022 Extended European Search Report dated Aug. 22, 2023.

U.S. Appl. No. 17/468,318, filed Sep. 7, 2021 Final Office Action dated Sep. 8, 2023.

U.S. Appl. No. 17/471,015, filed Sep. 9, 2021 Final Office Action dated Oct. 12, 2023.

U.S. Appl. No. 17/534,099, filed Nov. 23, 2021 Final Office Action dated Sep. 29, 2023.

(56) References Cited

OTHER PUBLICATIONS

U.S. Appl. No. 17/538,911, filed Nov. 30, 2021 Final Office Action dated Sep. 13, 2023.
U.S. Appl. No. 17/684,180, filed Mar. 1, 2022 Non-Final Office Action dated Jul. 28, 2023.
M. Ikhsan, K. K. Tan, AS. Putra, C. F. Kong, et al., "Automatic identification of blood vessel cross-section for central venous catheter placement using a cascading classifier," 39th Annual International Conference of the IEEE Engineering in Medicine and Biology Society (EMBC). pp. 1489-1492 (Year: 2017).
U.S. Appl. No. 17/471,015, filed Sep. 9, 2021 Non-Final Office Action dated Mar. 28, 2024.
U.S. Appl. No. 17/534,099, filed Nov. 23, 2021 Non-Final Office Action dated Mar. 14, 2024.
U.S. Appl. No. 17/538,911, filed Nov. 30, 2021 Notice of Allowance dated Mar. 14, 2024.
U.S. Appl. No. 17/684,180, filed Mar. 1, 2022 Advisory Action dated Apr. 4, 2024.
U.S. Appl. No. 17/684,180, filed Mar. 1, 2022 Non-Final Office Action dated May 8, 2024.
U.S. Appl. No. 17/894,460, filed Aug. 24, 2022 Advisory Action dated Apr. 4, 2024.
U.S. Appl. No. 17/979,564, filed Nov. 2, 2022 Non-Final Office Action dated Jun. 5, 2024.
U.S. Appl. No. 18/238,281, filed Aug. 25, 2023 Non-Final Office Action dated Mar. 22, 2024.
Thermographic venous blood flow characterization with external cooling stimulation (Year: 2018).
U.S. Appl. No. 17/534,099, filed Nov. 23, 2021 Notice of Allowance dated Sep. 18, 2024.
U.S. Appl. No. 17/538,943, filed Nov. 30, 2021 Notice of Allowance dated Aug. 14, 2024.
U.S. Appl. No. 17/684,180, filed Mar. 1, 2022 Final Office Action dated Sep. 23, 2024.
U.S. Appl. No. 17/722,111, filed Apr. 15, 2022 Final Office Action dated Jul. 12, 2024.
U.S. Appl. No. 17/894,460, filed Aug. 24, 2022 Non-Final Office Action dated Sep. 25, 2024.
U.S. Appl. No. 17/979,601, filed Nov. 2, 2022 Non-Final Office Action dated Aug. 20, 2024.
U.S. Appl. No. 17/987,698, filed Nov. 15, 2022 Non-Final Office Action dated Sep. 20, 2024.
U.S. Appl. No. 18/238,281, filed Aug. 25, 2023 Notice of Allowance dated Jul. 16, 2024.
PCT/US2022/045372 filed Sep. 30, 2022 International Search Report and Written Opinion dated Jan. 14, 2023.
PCT/US2024/037647 filed Jul. 11, 2024 International Search Report and Written Opinion dated Oct. 16, 2024.
U.S. Appl. No. 17/471,015, filed Sep. 9, 2021 Notice of Allowance dated Oct. 29, 2024.
U.S. Appl. No. 17/684,180, filed Mar. 1, 2022 Advisory Action dated Dec. 27, 2024.
U.S. Appl. No. 17/722,111, filed Apr. 15, 2022 Advisory Action dated Oct. 23, 2024.
U.S. Appl. No. 17/722,111, filed Apr. 15, 2022 Notice of Allowance dated Dec. 18, 2024.
U.S. Appl. No. 17/894,460, filed Aug. 24, 2022 Final Office Action dated Dec. 31, 2024.
U.S. Appl. No. 17/957,562, filed Sep. 30, 2022 Final Office Action dated Nov. 27, 2024.
U.S. Appl. No. 17/957,562, filed Sep. 30, 2022 Non-Final Office Action dated Jun. 20, 2024.
U.S. Appl. No. 17/973,171, filed Oct. 25, 2022 Non-Final Office Action dated Dec. 6, 2024.
U.S. Appl. No. 17/979,564, filed Nov. 2, 2022 Final Office Action dated Oct. 18, 2024.
U.S. Appl. No. 17/979,601, filed Nov. 2, 2022 Final Office Action dated Dec. 5, 2024.
U.S. Appl. No. 17/987,698, filed Nov. 15, 2022 Final Office Action dated Dec. 13, 2024.
U.S. Appl. No. 18/113,003, filed Feb. 22, 2023 Non-Final Office Action dated Nov. 27, 2024.
U.S. Appl. No. 18/121,802, filed Mar. 15, 2023 Non-Final Office Action dated Dec. 16, 2024.
Chen et al.,3D near infrared and ultrasound imaging of peripheral blood vessels for real-time localization and needle guidance. InMedical Image Computing and Computer-Assisted Intervention—MICCAI 2016 (pp. 388-396) (Year: 2016).
U.S. Appl. No. 17/684,180, filed Mar. 1, 2022 Final Office Action dated May 29, 2025.
U.S. Appl. No. 17/684,180, filed Mar. 1, 2022 Non-Final Office Action dated Jan. 17, 2025.
U.S. Appl. No. 17/894,460, filed Aug. 24, 2022 Advisory Action dated Mar. 13, 2025.
U.S. Appl. No. 17/957,562, filed Sep. 30, 2022 Advisory Action dated Feb. 12, 2025.
U.S. Appl. No. 17/957,562, filed Sep. 30, 2022 Examiner's Answer dated Jun. 16, 2025.
U.S. Appl. No. 17/973,171, filed Oct. 25, 2022 Final Office Action dated Apr. 3, 2025.
U.S. Appl. No. 17/979,564, filed Nov. 2, 2022 Advisory Action dated Jan. 17, 2025.
U.S. Appl. No. 17/979,564, filed Nov. 2, 2022 Examiner's Answer dated May 30, 2025.
U.S. Appl. No. 17/979,601, filed Nov. 2, 2022 Advisory Action dated Feb. 11, 2025.
U.S. Appl. No. 17/979,601, filed Nov. 2, 2022 Notice of Allowance dated Mar. 27, 2025.
U.S. Appl. No. 17/987,698, filed Nov. 15, 2022 Advisory Action dated Feb. 21, 2025.
U.S. Appl. No. 17/987,698, filed Nov. 15, 2022 Non-Final Office Action dated May 23, 2025.
U.S. Appl. No. 18/113,003, filed Feb. 22, 2023 Final Office Action dated Apr. 29, 2025.
U.S. Appl. No. 18/121,802, filed Mar. 15, 2023 Notice of Allowance dated Jun. 5, 2025.
U.S. Appl. No. 18/221,318, filed Jul. 12, 2023 Non-Final Office Action dated Jun. 23, 2025.
U.S. Appl. No. 18/221,318, filed Jul. 12, 2023 Restriction Requirement dated Mar. 28, 2025.
U.S. Appl. No. 18/674,601, filed May 24, 2024 Non-Final Office Action dated Jan. 7, 2025.
U.S. Appl. No. 18/674,601, filed May 24, 2024 Notice of Allowance dated Mar. 26, 2025.
U.S. Appl. No. 17/684,180, filed Mar. 1, 2022 Notice of Allowance dated Sep. 30, 2025.
U.S. Appl. No. 17/894,460, filed Aug. 24, 2022 Examiner's Answer dated Oct. 2, 2025.
U.S. Appl. No. 18/221,318, filed Jul. 12, 2023 Final Office Action dated Oct. 14, 2025.
U.S. Appl. No. 18/936,351, filed Nov. 4, 2024 Non-Final Office Action dated Nov. 10, 2025.
Konica Minolta, "Vascular NAVI" product website. https://www.konicaminolta.com/global-en/healthcare/technology/ultrasound/vascularnavi/index.html. Last accessed Jun. 2025.
U.S. Appl. No. 17/684,180, filed Mar. 1, 2022 Advisory Action dated Aug. 22, 2025.
U.S. Appl. No. 17/973,171, filed Oct. 25, 2022 Advisory Action dated Jun. 30, 2025.
U.S. Appl. No. 17/987,698, filed Nov. 15, 2022 Final Office Action dated Sep. 12, 2025.
U.S. Appl. No. 18/113,003, filed Feb. 22, 2023 Advisory Action dated Jul. 2, 2025.
U.S. Appl. No. 18/113,003, filed Feb. 22, 2023 Notice of Allowance dated Aug. 15, 2025.
PCT/US2022/025097 filed Apr. 15, 2021 International Preliminary Report on Patentability dated Oct. 26, 2023.
PCT/US2023/030970 filed Aug. 23, 2023 International Search Report and Written Opinion dated Oct. 30, 2023.
U.S. Appl. No. 17/468,318, filed Sep. 7, 2021 Advisory Action dated Nov. 6, 2023.
U.S. Appl. No. 17/468,318, filed Sep. 7, 2021 Notice of Allowance dated Jan. 18, 2024.

(56) References Cited

OTHER PUBLICATIONS

U.S. Appl. No. 17/471,015, filed Sep. 9, 2021 Advisory Action dated Feb. 2, 2024.
U.S. Appl. No. 17/534,099, filed Nov. 23, 2021 Advisory Action dated Dec. 8, 2023.
U.S. Appl. No. 17/538,911, filed Nov. 30, 2021 Advisory Action dated Nov. 22, 2023.
U.S. Appl. No. 17/538,943, filed Nov. 30, 2021 Non-Final Office Action dated Jan. 30, 2024.
U.S. Appl. No. 17/684,180, filed Mar. 1, 2022 Final Office Action dated Jan. 18, 2024.
U.S. Appl. No. 17/722,111, filed Apr. 15, 2022 Non-Final Office Action dated Dec. 22, 2023.
U.S. Appl. No. 17/894,460, filed Aug. 24, 2022 Final Office Action dated Jan. 31, 2024.
U.S. Appl. No. 17/894,460, filed Aug. 24, 2022 Non-Final Office Action dated Nov. 6, 2023.
U.S. Appl. No. 17/894,460, filed Aug. 24, 2022 Non-Final Office Action dated Jan. 14, 2026.
U.S. Appl. No. 17/973,171, filed Oct. 25, 2022 Examiner's Answer dated Jan. 28, 2026.
U.S. Appl. No. 17/979,564, filed Nov. 2, 2022 Board Decision dated Mar. 4, 2026.
U.S. Appl. No. 17/987,698, filed Nov. 15, 2022 Advisory Action dated Nov. 21, 2025.
U.S. Appl. No. 17/987,698, filed Nov. 15, 2022 Non-Final Office Action dated Mar. 16, 2026.
U.S. Appl. No. 19/042,983, filed Jan. 31, 2025 Notice of Allowance dated Feb. 24, 2026.
Sonka, Momodou L., T. Campbell Arnold, and Ivan A. Kuznetsov. "Machine learning in point of care ultrasound." POCUS journal 7. Kidney (2022): 78. (Year: 2022).
U.S. Appl. No. 17/957,562, filed Sep. 30, 2022 Board Decision dated Apr. 22, 2026.
U.S. Appl. No. 17/957,562, filed Sep. 30, 2022 Notice of Allowance dated May 1, 2026.
U.S. Appl. No. 17/979,564, filed Nov. 2, 2022 Notice of Allowance dated May 29, 2026.
U.S. Appl. No. 17/987,698, filed Nov. 15, 2022 Final Office Action dated Jun. 25, 2026.
U.S. Appl. No. 18/221,318, filed Jul. 12, 2023 Non-Final Office Action dated May 6, 2026.
U.S. Appl. No. 18/936,351, filed Nov. 4, 2024 Notice of Allowance dated Jun. 10, 2026.
U.S. Appl. No. 19/058,331, filed Feb. 20, 2025 Notice of Allowance dated Apr. 20, 2026.
U.S. Appl. No. 19/251,382, filed Jun. 26, 2025 Restriction Requirement dated May 18, 2026.

* cited by examiner

MEDICAL DEVICE SYSTEM HAVING BLOOD VESSEL CORRELATION TOOLS

PRIORITY

This application claims the benefit of priority to U.S. Provisional Application No. 63/175,484, filed Apr. 15, 2021, which is incorporated by reference in its entirety into this application.

BACKGROUND

Readily detecting and accessing a blood vessel can require a user to detect the blood vessel in one location and confirm different parameters of the detected blood vessel in another distinct location. Clinicians may use an ultrasound probe to detect one or more blood vessels within a target area but have to confirm different parameters of the blood vessels on a screen, breaking the clinician's focus from the target area to the screen. It would be beneficial for clinicians to have access to blood vessel visualization or blood vessel detection data close to or within the target area, allowing the clinicians to focus their full attention on the target area. Disclosed herein are a medical device system having blood vessel correlation tools and method of use that address the foregoing

SUMMARY

Disclosed herein is a medical device system configured to detect one or more blood vessels within a target area. The medical device system includes an ultrasound probe configured to detect one or more blood vessels, the ultrasound probe in communication with a console. The medical device system further includes one or more blood vessel correlation tools configured to generate a local output detectable by a user. The one or more blood vessel correlation tools are coupled to the ultrasound probe and in communication with a console. The one or more blood vessel correlation tools are selected from the group consisting of a light array, one or more visible light projectors, a haptic feedback system, and an auditory device.

In some embodiments, the ultrasound probe is configured to detect the one or more blood vessels within the target area using ultrasound or near-infrared reflection differentiation.

In some embodiments, the console includes one or more processors, an energy source, non-transitory computer readable medium and a plurality of logic modules.

In some embodiments, the plurality of logic modules, when activated by the processor, are configured to perform operations including receiving detected blood vessel data from the ultrasound probe, correlating the detected blood vessel data with the local output corresponding to one or more parameters of the detected blood vessels, and generating the local output that is detected by a user.

In some embodiments, the one or more parameters include blood vessel location within the target area, blood vessel size, blood vessel type, blood vessel depth or vascular access devices that are configured to access the one or more blood vessels.

In some embodiments, the local output includes visible illumination of one or more lights in the light array, and the visible illumination of the one or more lights in the light array includes visible illumination of a different color, a different pattern, or of varied brightness corresponding to the one or more parameters of the detected blood vessels.

In some embodiments, the local output includes one or more visible light projections by the one or more visible light projectors on the target area.

In some embodiments, the one or more visible light projections display a blood vessel visualization depiction.

In some embodiments, the one or more visible light projections display different colors, different shapes, or varied brightness corresponding to the one or more parameters of the detected blood vessels.

In some embodiments, the local output includes an auditory signal from the auditory device.

In some embodiments, the auditory device emits sonic tones of various frequencies, various patterns, or various pitches corresponding to the one or more parameters of the detected blood vessels.

In some embodiments, the local output includes vibrations of a portion of the ultrasound probe through the haptic feedback system.

In some embodiments, the haptic feedback system vibrates in various patterns, various frequencies or various magnitudes corresponding to the one or more parameters of the detected blood vessels.

Also disclosed herein is a method of detecting one or more blood vessels within a target area and generating a local output detected by a user. The method includes detecting one or more blood vessels within a target area using an ultrasound probe, correlating detected blood vessel data with a local output corresponding to one or more parameters of the detected blood vessels, and generating the local output configured to be detected by a user using one or more blood vessel correlation tools.

In some embodiments, detecting one or more blood vessels in a target area includes using an ultrasound probe configured to detect the one or more blood vessels by ultrasound waves or near-infrared reflection differentiation.

In some embodiments, correlating detected blood vessel data with a local output corresponding to one or more parameters of the detected blood vessels includes the one or more parameters including blood vessel location, blood vessel type, blood vessel size, and vascular access devices configured to access the detected blood vessels.

In some embodiments, generating the local output configured to be detected by a user using one or more blood vessel correlation tools includes the one or more blood vessel correlation tools including a light array, one or more visible light projectors, a haptic feedback system, or an auditory device.

In some embodiments, the local output includes one or more lights in the light array being illuminated a different color, a different pattern, or a varied brightness, each of the different colors, patterns, or brightness corresponding to one parameter of the one or more parameters.

In some embodiments, the local output includes one or more blood vessel visualization depictions projected on the target area by the one or more visible light projectors, the one or more blood vessel visualization depictions including different colors or different shapes, each of the different colors or shapes corresponding to one parameter of the one or more parameters.

In some embodiments, the local output includes the haptic feedback system vibrating a portion of the ultrasound probe in various patterns, various frequencies, or various magnitudes, each of the various patterns, frequencies, or magnitudes corresponding to one parameter of the one or more parameters.

In some embodiments, the local output includes the auditory device emitting one or more sonic tones having various frequencies, pitches, or patterns, each of the various frequencies, pitches or patterns corresponding to one parameter of the one or more parameters.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
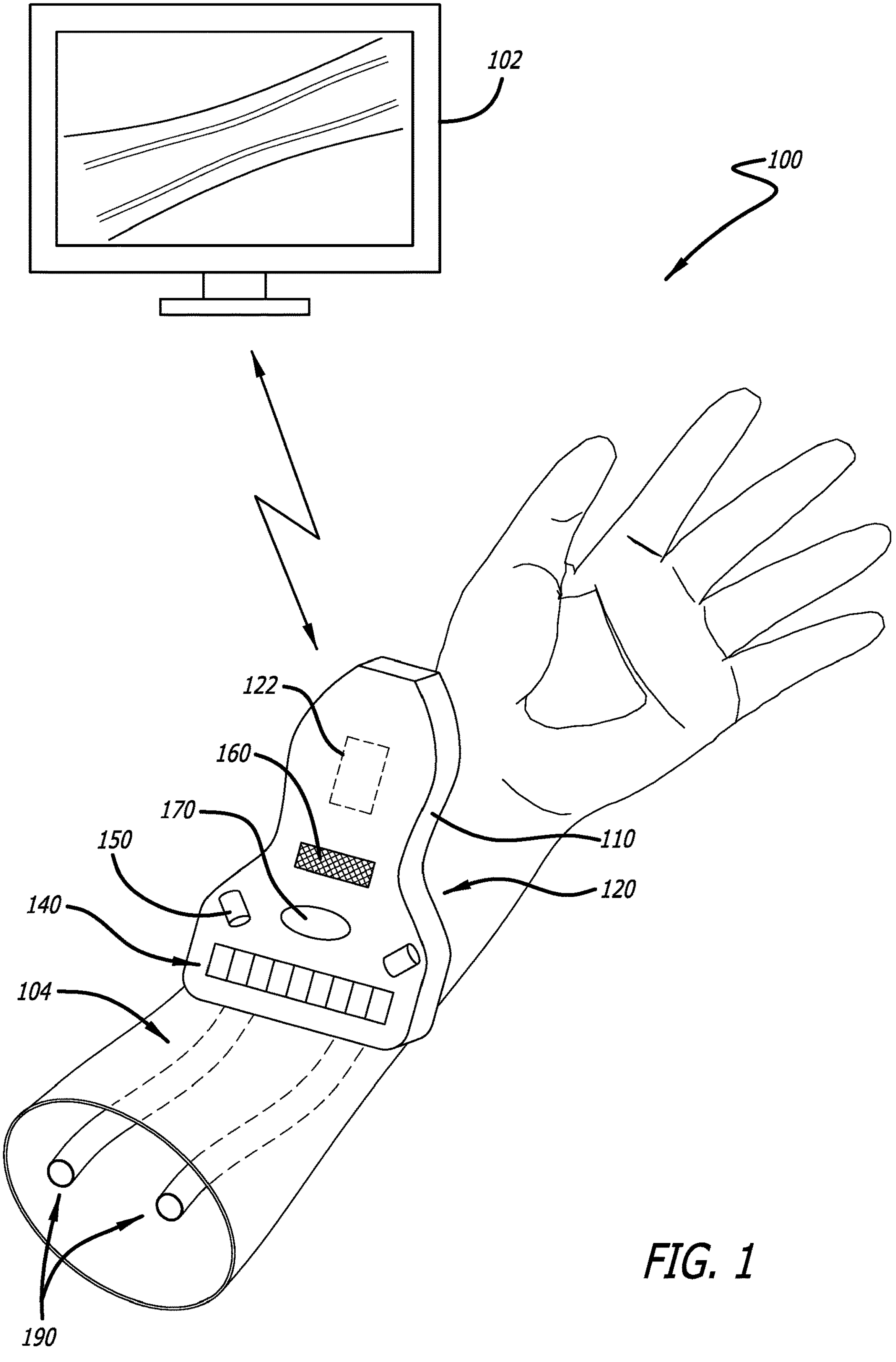
FIG. 1 illustrates a perspective view of a medical device system including an ultrasound probe having one or more ultrasound vessel correlation tools, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, an ultrasound probe disclosed herein includes a portion of the ultrasound probe intended to be near a clinician when the ultrasound probe is used on a patient. Likewise, a "proximal length" of, for example, the ultrasound probe includes a length of the ultrasound probe intended to be near the clinician when the ultrasound probe is used on the patient. A "proximal end" of, for example, the ultrasound probe includes an end of the ultrasound probe intended to be near the clinician when the ultrasound probe is used on the patient. The proximal portion, the proximal-end portion, or the proximal length of the ultrasound probe can include the proximal end of the ultrasound probe; however, the proximal portion, the proximal-end portion, or the proximal length of the ultrasound probe need not include the proximal end of the ultrasound probe. That is, unless context suggests otherwise, the proximal portion, the proximal-end portion, or the proximal length of the ultrasound probe is not a terminal portion or terminal length of the ultrasound probe.

With respect to "distal," a "distal portion" or a "distal-end portion" of, for example, an ultrasound probe disclosed herein includes a portion of the ultrasound probe intended to be near or in a patient when the ultrasound probe is used on the patient. Likewise, a "distal length" of, for example, the ultrasound probe includes a length of the ultrasound probe intended to be near or in the patient when the ultrasound probe is used on the patient. A "distal end" of, for example, the ultrasound probe includes an end of the ultrasound probe intended to be near or in the patient when the ultrasound probe is used on the patient. The distal portion, the distal-end portion, or the distal length of the ultrasound probe can include the distal end of the ultrasound probe; however, the distal portion, the distal-end portion, or the distal length of the ultrasound probe need not include the distal end of the ultrasound probe. That is, unless context suggests otherwise, the distal portion, the distal-end portion, or the distal length of the ultrasound probe is not a terminal portion or terminal length of the ultrasound probe.

Unless defined otherwise, all technical and scientific terms used herein have the same meaning as commonly understood by those of ordinary skill in the art.

FIG. 1 illustrates a perspective view of a medical device system 100 including one or more blood vessel correlation tools 120, in accordance with some embodiments. In some embodiments, the medical device system 100 includes an ultrasound probe 110 configured to detect one or more blood vessels 190 in a target area 104. In some embodiments, the ultrasound probe 110 may be in communication with a display screen 102 configured to display a depiction of the one or more detected blood vessels 190 in the target area 104. In some embodiments, the ultrasound probe 110 may be in wireless communication with the display screen 102. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like.

In some embodiments, the ultrasound probe 110 may include one or more blood vessel correlation tools 120 thereon. The one or more blood vessel correlation tools 120 may be in communication with the ultrasound probe 110. The one or more blood vessel correlation tools 120 may be configured to receive the one or more detected blood vessel data from the ultrasound probe 110. The one or more blood vessel correlation tools 120 may be configured to correlate the detected blood vessel data with a location of the one or more blood vessels within the target area 104. The one or more blood vessel correlation tools 120 may be configured to generate a local output that can be detected by a user, the local output indicating one or more detected parameters of the detected blood vessels 190. In some embodiments, the ultrasound probe 110 may be configured to detect the one or more blood vessels 190 by ultrasound waves. In some embodiments, the ultrasound probe 110 may be configured to detect the one or more blood vessels 190 by near infrared reflection differentiation using a near infrared or infrared emitter and detector.

The one or more blood vessel correlation tools 120 may include any one or more of the following: a single light or a light array 140, one or more visible light projectors 150, a haptic feedback system 160, and an auditory device 170. The one or more blood vessel correlation tools 120 may be in communication with a console 122 configured to provide communication between the ultrasound probe 110 and the one or more blood vessel correlation tools 120. In some embodiments, the local output may include a local visual output, a local haptic output, a local auditory output, or a combination thereof. The local output may indicate one or more parameters including blood vessel type (e.g., vein or artery), blood vessel size (e.g., diameter, cross sectional area, or the like), blood vessel location, blood vessel depth, or appropriate vascular access device that may access the detected blood vessels 190. Advantageously, the local output of the medical device system 100 allows the user to focus their entire attention on the target area 104 and receive data on the various parameters of the detected one or more blood vessels 190 near the target area 104 or within the target area 104 instead of receiving data the various parameters of the detected one or more blood vessels on the display screen 102 away from the target area 104.

Figure 2:
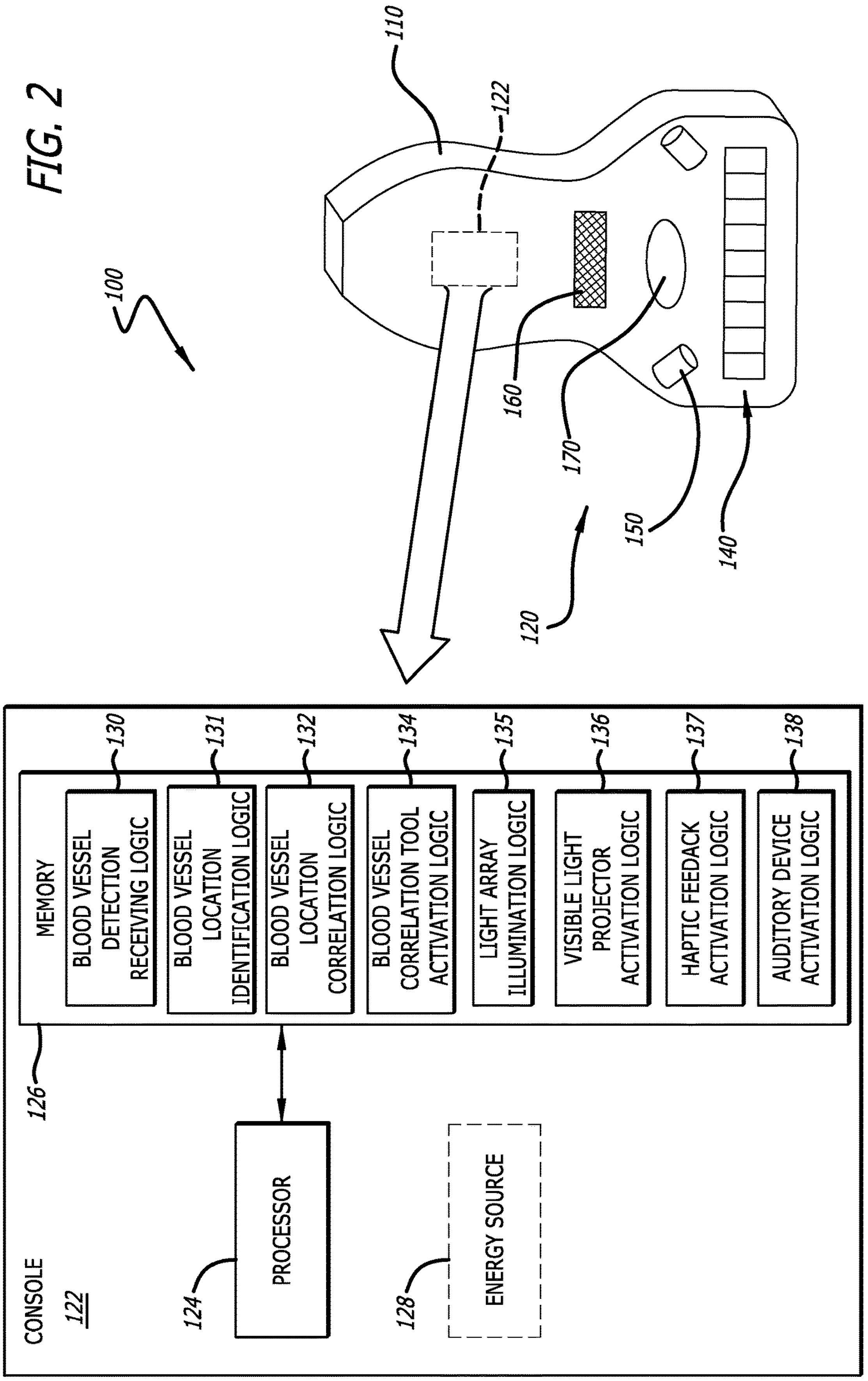
FIG. 2 illustrates a block diagram of some components of the medical device system including the ultrasound probe and a console, in accordance with some embodiments.

FIG. 2 illustrates a block diagram of some components of the medical device system 100 including the ultrasound probe 110 and the console 122, in accordance with some embodiments. In some embodiments, the ultrasound probe 110 of the medical device system 100 includes the console 122 therein configured to control the one or more vessel correlation tools 120. In some embodiments, the console 122 includes one or more processors 124, non-transitory computer readable medium ("memory") 126, an energy source 128 and a plurality of logic modules. The console 122 is in communication with the ultrasound probe 110 and each of the one or more blood vessel correlation tools 120. The plurality of logic modules may be configured to include one or more of: a blood vessel detection receiving logic 130, a blood vessel location identification logic 131, a blood vessel location correlation logic 132, and a blood vessel correlation tool activation logic 134. In some embodiments, the blood vessel detection receiving logic 130 may be configured to receive the blood vessel detection data from the ultrasound probe 110.

In some embodiments, the blood vessel detection data may include the detected ultrasound wave data or the detected near-infrared reflection differentiation data. In some embodiments, the blood vessel location identification logic 131 may be configured to identify the location of the one or more blood vessels 190 from the detected blood vessel data. In some embodiments, the blood vessel location identification logic 131 may be configured to identify the location of the one or more blood vessels 190 within one or more captured images from the ultrasound probe 110. In some embodiments, the blood vessel location identification logic 131 may be configured to identify the location of the one or more blood vessels 190 within the target area 104. In some embodiments, the blood vessel location correlation logic 132 may be to correlate the location of the one or more blood vessels 190 within the target area 104 in generating the local output. In some embodiments, the blood vessel correlation tool activation logic 134 may be configured to activate the one or more blood vessel correlation tools 120 to indicate to a user, the location of the one or more blood vessels 190 within the target area 104. In some embodiments, the blood vessel correlation tool activation logic 134 may be configured to simultaneously activate two or more of the blood vessel correlation tools 120. In some embodiments, activating the one or more blood vessel correlation tools 120 generates the local output configured to be detected by the user, the local output identifying one or more parameters of the detected blood vessels 190 in the target area 104. In some embodiments, simultaneously activating two or more blood vessel correlation tools generates two or more distinct local outputs configured to identify, to the user, two or more parameters of the detected blood vessels 190. In some embodiments, the two or more local outputs may be configured to identify the same two or more parameters of the detected blood vessels 190 or different parameters of the detected blood vessels 190.

In some embodiments, the blood vessel correlation tool activation logic 134 may include sub-logic specific to the blood vessel correlation tool used. For example, the sub-logic may be configured to include a light array illumination logic 135, a visible light projection activation logic 136, a haptic feedback activation logic 137, and an auditory device activation logic 138. In some embodiments, the light array illumination logic 135 may be configured to illuminate one or more of the lights within the light array 140. In some embodiments, the light array illumination logic 135 may be configured to illuminate the one or more lights within the light array 140 different colors to identify different blood vessel types (e.g., artery versus vein) or differing blood vessel sizes (e.g., cross sectional area), indicating an appropriate vascular access device for the detected blood vessel 190. In some embodiments, the light array illumination logic 135 may be configured to vary the brightness of the one or more lights within the light array 140 to indicate different blood vessel depth, different blood vessel size or the like.

In some embodiments, the visible light projection activation logic 136 may be configured to project a depiction of the detected blood vessels 190 within the target area 104, including on a skin surface. In some embodiments, the visible light projection activation logic 136 may be configured to vary the projected depiction of the detected blood vessels 190 within the target area 104 by varying the shape, the location, the color, or the brightness of the depiction to indicate different blood vessel depth, different blood vessel size, different blood vessel type, different blood vessel location or different vascular access devices that may access the detected blood vessels 190.

In some embodiments, the haptic feedback activation logic 137 may be configured to provide haptic feedback to the user through vibration of a portion of the ultrasound probe 110 including the haptic feedback system 160. In some embodiments, the haptic feedback activation logic 137 may be configured to vary a vibration pulse by vibration pulse frequency and/or vibration pulse intensity to indicate different blood vessel depth, different blood vessel size, different blood vessel type, different blood vessel location or different vascular access devices that may access the detected blood vessels 190.

In some embodiments, the auditory device activation logic 138 may be configured to provide one or more auditory signals from the auditory device 170. In some embodiments, the auditory signals may include one or more sonic tones, instructions of the location of the blood vessels 190 within the target area 104, or other auditory signals. In some embodiments, the auditory device activation logic 138 may be configured to vary the one or more auditory signals from the auditory device 170 by varying sonic tone frequency, sonic tone pitch, or sonic tone intensity to indicate to the user different blood vessel depth, different blood vessel size, different blood vessel type, different blood vessel location or different vascular access devices that may access the detected blood vessels 190.

Figure 3B:
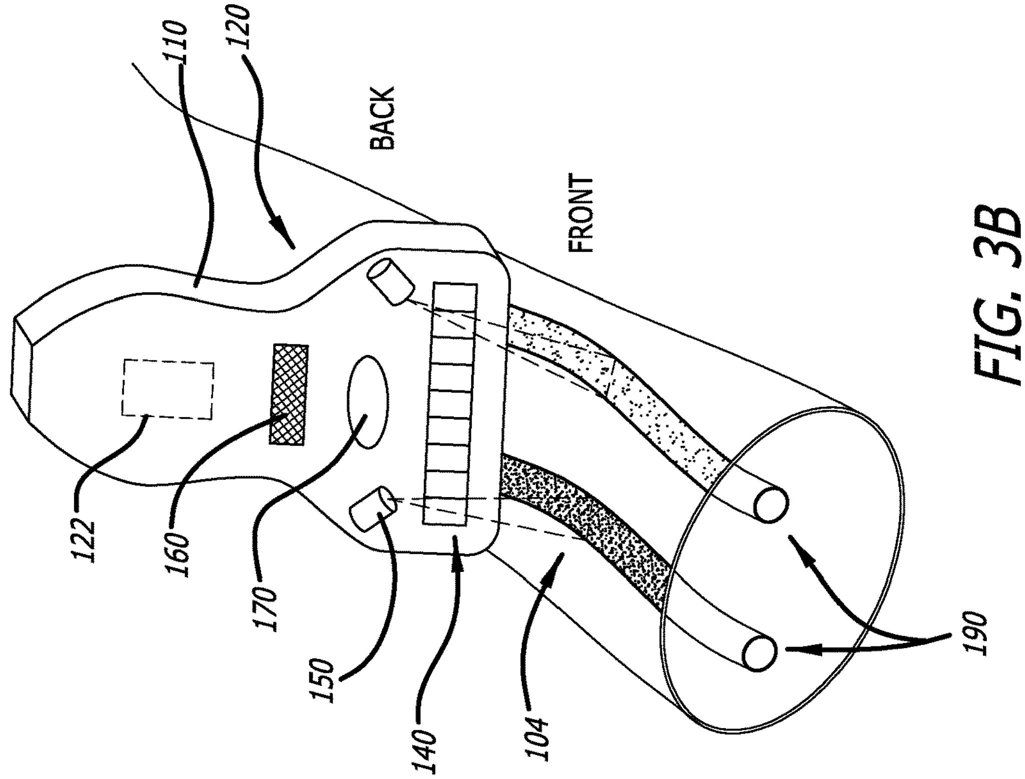
FIG. 3B illustrates a perspective view of the ultrasound probe including one or more visible light projectors, in accordance with some embodiments.
Figure 3A:
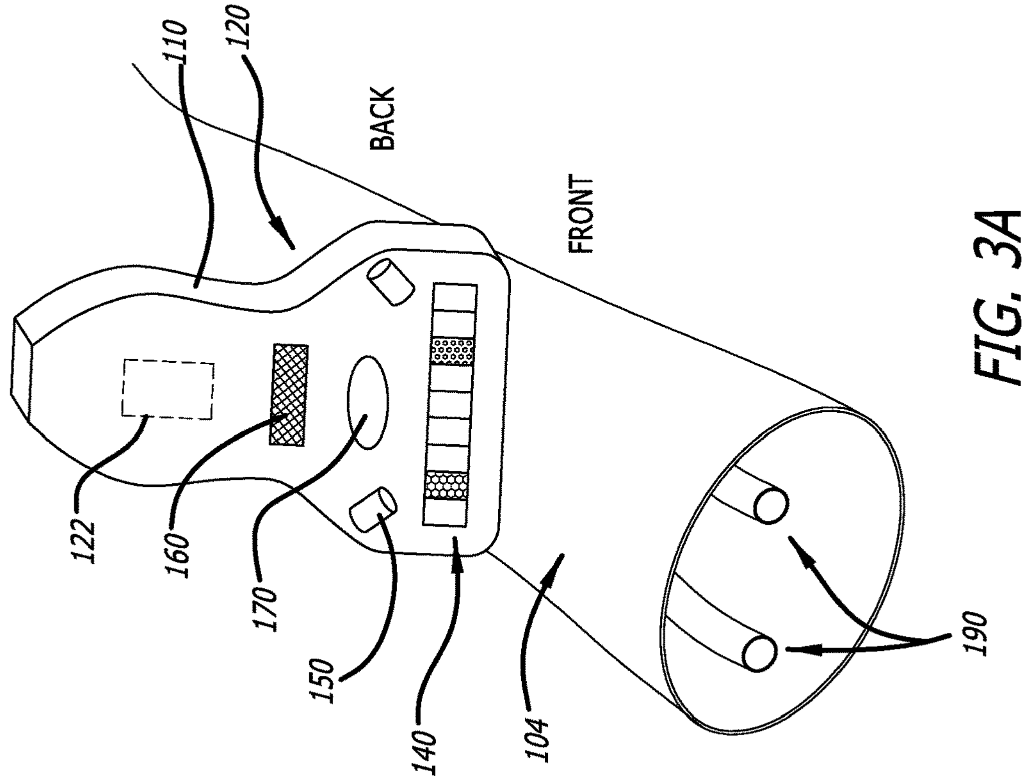
FIG. 3A illustrates a perspective view of the ultrasound probe including a light array, in accordance with some embodiments.

FIG. 3A illustrates a perspective view of the ultrasound probe 110 including the light array 140 coupled thereto, in accordance with some embodiments. In some embodiments, the single light or the light array 140 may be coupled to the ultrasound probe 110. In some embodiments, the light array 140 may be detachably coupled to the probe 110. In some embodiments, the light array 140 may be coupled to a front surface or a back surface, orientating the ultrasound probe 110 for proper use. The light array 140 includes a plurality of individual lights arranged in an array. In some embodiments, the individual lights may include light-emitting diodes ("LEDs"). The light array 140 may be configured to indicate the location of the one or more blood vessels 190 within the target area 104. The individual lights or multiple sequential lights in the light array 140 may be illuminated, as the local output, to indicate the location of the one or more blood vessels 190 directly below the light array 140. In some embodiments, the illuminated lights in the light array 140 may be configured to indicate to the user, other parameters of the one or more detected blood vessels 190. For example, the lights within the light array 140 may be illuminated different colors and varied brightness to correspond to different blood vessel types (e.g., artery versus vein), different blood vessel sizes, different blood vessel depth or different vascular access devices that may be configured to access the one or more blood vessels 190.

FIG. 3B illustrates a perspective view of the ultrasound probe 110 including the one or more visible light projectors 150 coupled thereto, in accordance with some embodiments. In some embodiments, the one or more visible light projectors 150 may be coupled to the ultrasound probe 110 or embedded within the ultrasound probe 110. In some embodiments, the one or more visible light projectors 150 may be configured to display various visible light projections on the target area 104 including on a skin surface within the target area 104. In some embodiments, each visible light projector 150 may be configured to project one visible light projection within the target area or the visible light projectors 150 may be configured to combine to project one visible light projection within the target area 104. In some embodiments, the one or more visible light projectors 150 may include one or more lasers. In some embodiments, the visible light projections may include one or more blood vessel visualization depictions. In some embodiments, the visible light projections may include various shapes or text. In some embodiments, the one or more visible light projections may be distinct, corresponding to different parameters of the one or more blood vessels. In some embodiments, the one or more visible light projections may be configured to display projections of different colors or of different brightness. In some embodiments, the different colors or different brightness may correspond to different blood vessel types, different blood vessel sizes, different blood vessel depth or different vascular access devices that may be configured to access the one or more blood vessels 190.

Figure 3D:
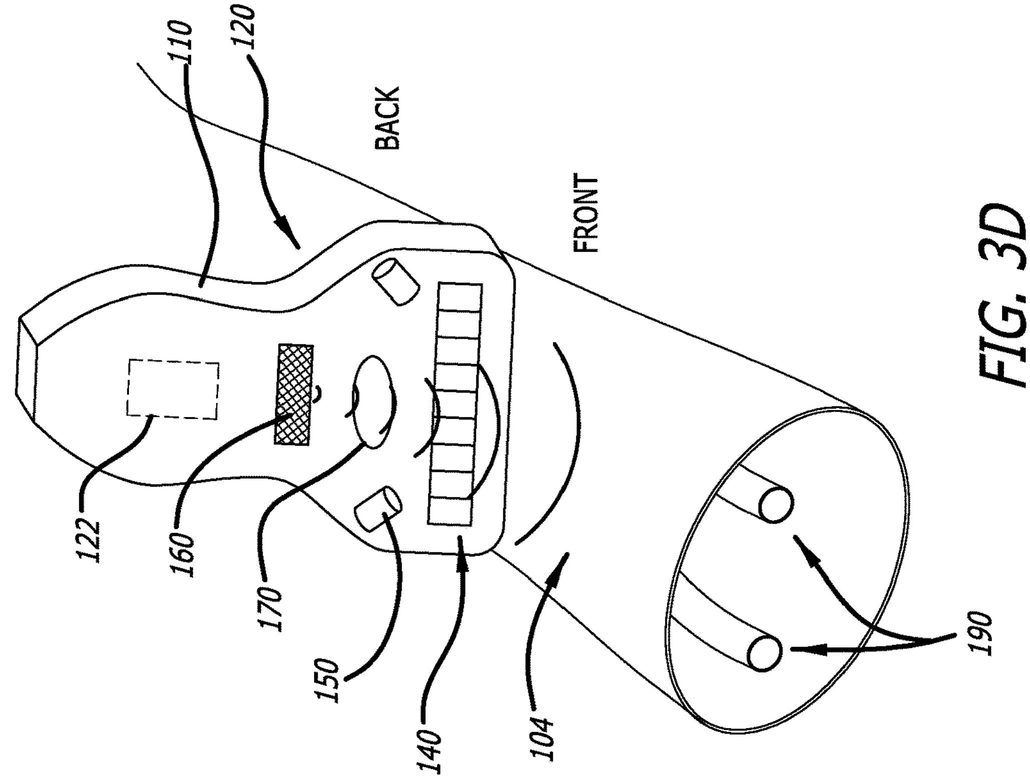
FIG. 3D illustrates a perspective view of the ultrasound probe including an auditory device, in accordance with some embodiments.
Figure 3C:
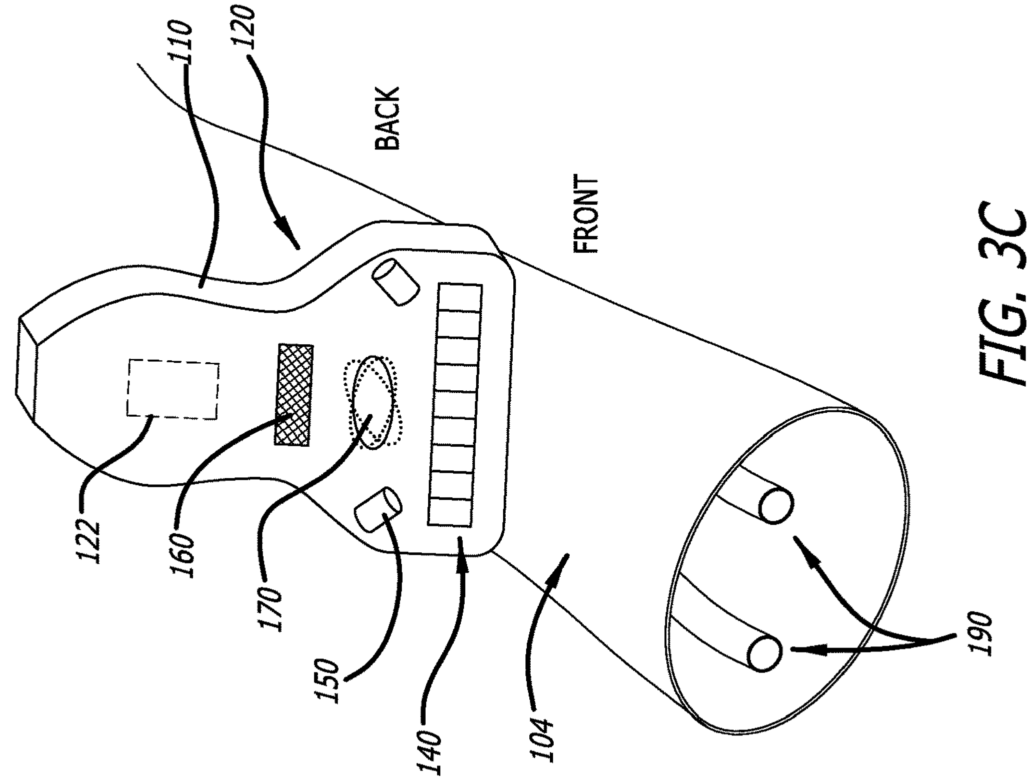
FIG. 3C illustrates a perspective view of the ultrasound probe including a haptic feedback system, in accordance with some embodiments.

FIG. 3C illustrates a perspective view of the ultrasound probe 110 including the haptic feedback system 160 in accordance with some embodiments. In some embodiments, the one or more blood vessel correlation tools 120 may include the haptic feedback system 160 configured to indicate the location of one or more blood vessels 190 to the user. In some embodiments, the haptic feedback system 160 may be configured to indicate other parameters of the detected blood vessels including blood vessel depth, blood vessel size, blood vessel type, or different vascular access devices that may be configured to access the one or more blood vessels 190. In some embodiments, the haptic feedback system 160 may be configured to indicate the parameters of the one or more blood vessels 190 through varied frequency or varied magnitude of pulses or vibrations.

FIG. 3D illustrates a perspective view of the ultrasound probe 110 including the auditory device 170, in accordance with some embodiments. In some embodiments, the one or more blood vessel correlation tools 120 may include the auditory device 170 coupled to the ultrasound probe 110. In some embodiments, the auditory device 170 may include a speaker in communication with the console 122. In some embodiments, the auditory device 170 may be integrated into the ultrasound probe 110. The auditory device 170 may be configured to identify the one or more blood vessels 190 to the user, using various sounds (e.g., auditory messages or the like) or sonic tones that may be varied in frequency or pitch. In some embodiments, the auditory device 170 may be configured to indicate other parameters of the blood vessels 190 to the user, including blood vessel depth, blood vessel size, blood vessel type or different vascular access devices that may be configured to access the one or more blood vessels 190.

Figure 4C:
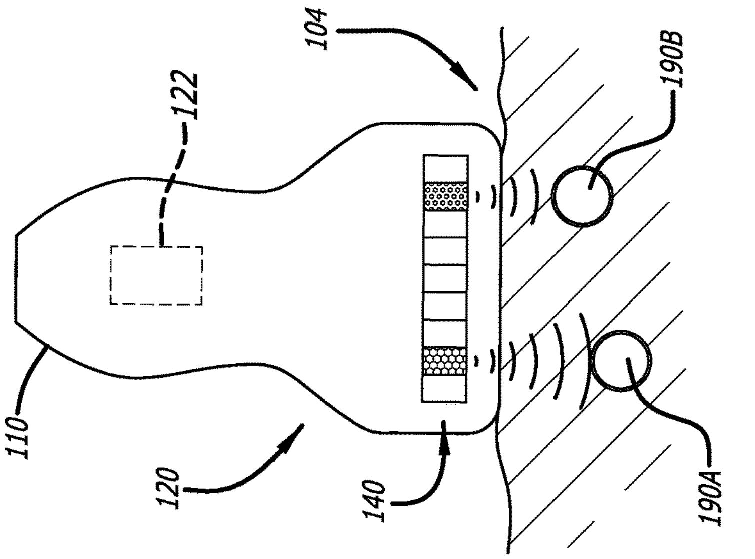
FIGS. 4A-4C illustrate a cross sectional view of an exemplary method of detecting one or more blood vessels within a target area and generating a local output configured to be detected by a user, in accordance with some embodiments.
Figure 4B:
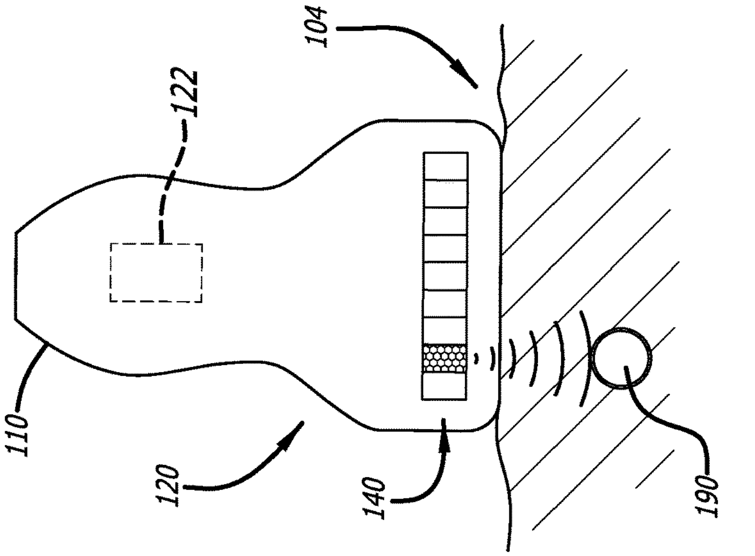
Figure 4A:
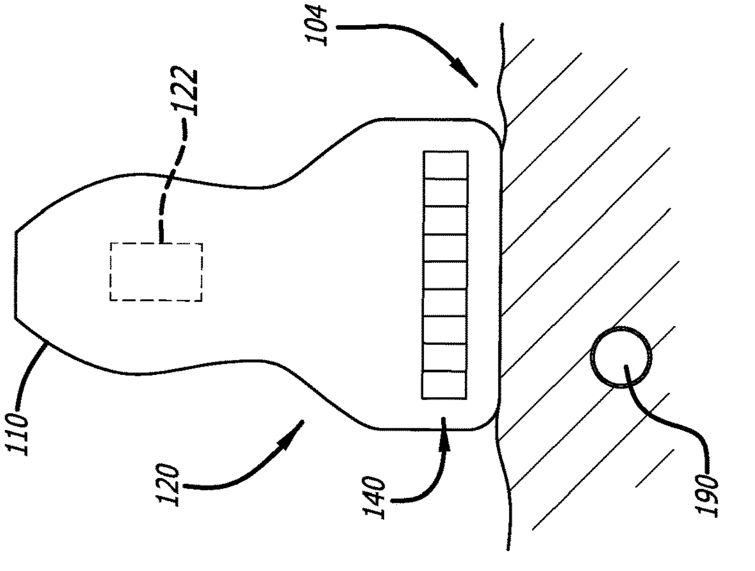

FIGS. 4A-4C illustrate a cross sectional view of detecting one or more blood vessels 190 within the target area 104 and generating a local output configured to be detected by a user, in accordance with some embodiments. As illustrated in FIG. 4A, the ultrasound probe 110 may be used to detect one or more blood vessels 190 within the target area 104. The ultrasound probe 110 may detect the one or more blood vessels 190 by ultrasound. The console 122 may correlate one of the parameters of the detected blood vessel 190 with a local output, the local output being transmitted to the one of the blood vessel correlation tools 120. As illustrated in FIG. 4B, the blood vessel correlation tool 120 illustrated includes the light array 140. The console 122 may illuminate one of the lights in the light array 140 a first color, indicating the location of the detected blood vessel 190 within the target area 104. The console 122 may illuminate one of the lights in a particular pattern to indicate the depth of the detected blood vessel 190. As illustrated in FIG. 4C, when the ultrasound probe 110 detects the first blood vessel 190A and the second blood vessel 190B within the target area 104, the console 122 may illuminate one of the lights in the light array 140 a first color and another light in the light array 140 a second color, both colors indicating the location of the first and second blood vessels 190A-190B within the target area 104. The console 122 may illuminate each light in the light array 140 a different pattern, to indicate the depth of the first detected blood vessel 190A versus the depth of the second detected blood vessel 190B.

Figure 5:
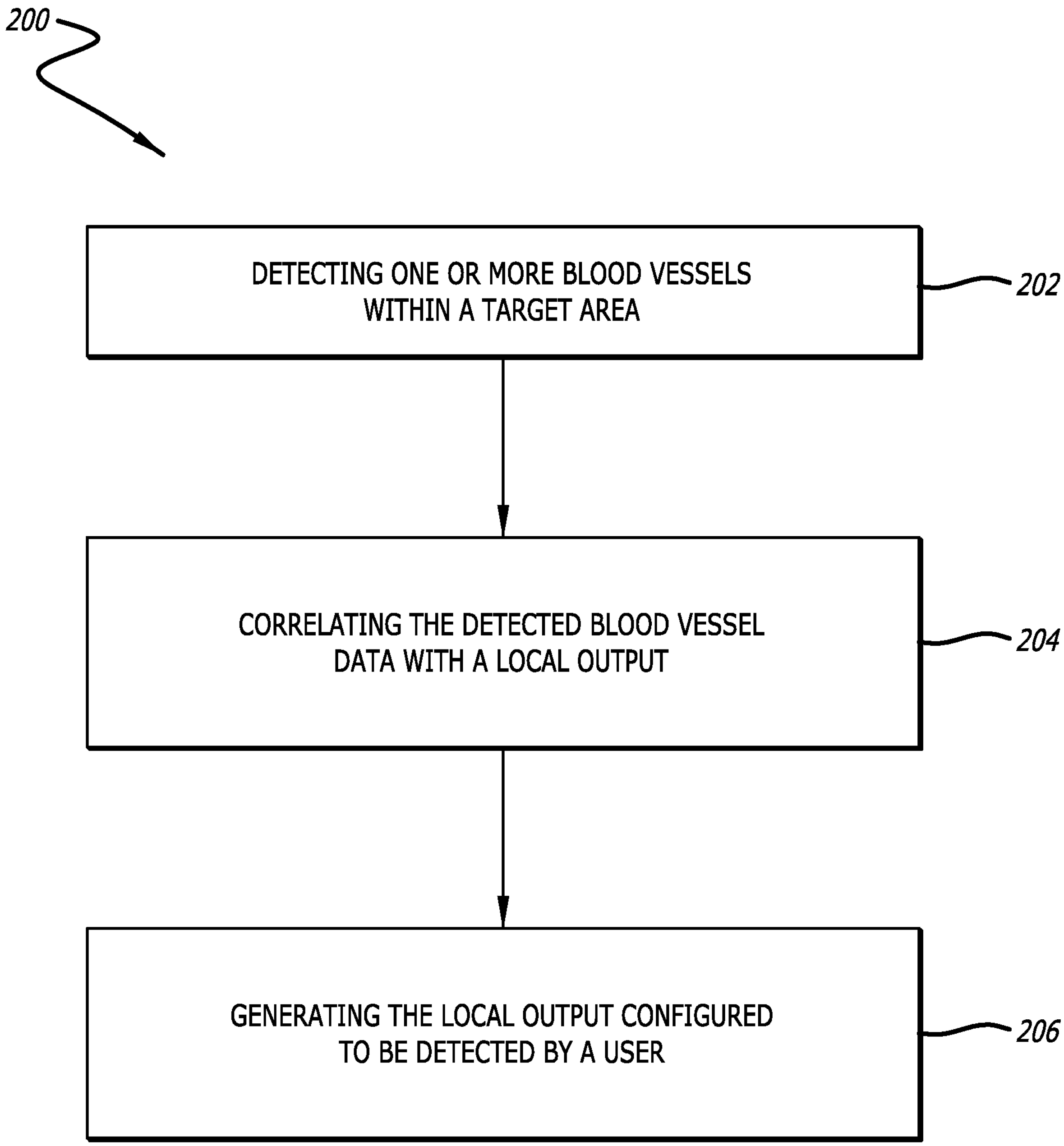
FIG. 5 illustrates a flow chart of the exemplary method of detecting one or more blood vessels within a target area and correlating the detected blood vessels with a local output detected by a user, in accordance with some embodiments.

FIG. 5 illustrates a flow chart of the exemplary method 200 of detecting one or more blood vessels 190 within a target area 104 and correlating the detected blood vessels 190 with a local output detected by a user, in accordance with some embodiments. In some embodiments, the method 200 includes detecting one or more blood vessels 190 within a target area 104 (block 202). In some embodiments, detecting the one or more blood vessels 190 within the target area 104 includes detecting using the ultrasound probe 110 configured to detect using ultrasound or near-infrared reflection differentiation.

The method 200 further includes correlating detected blood vessel data with a local output corresponding to one or more parameters of the detected blood vessels (block 204). In some embodiments, the local output may correspond to one or more parameters of the detected blood vessels 190. In some embodiments, the one or more parameters may include blood vessels type, blood vessel size, blood vessel depth, blood vessel location or vascular access devices configured to access the detected blood vessels 190. In some embodiments, correlating the detected blood vessel data includes the console 122 receiving the detected blood vessel data from the ultrasound probe 110.

The method 200 includes generating the local output configured to be detected by a user using one or more blood vessel correlation tools 120 (block 206). In some embodiments, the one or more blood vessel correlation tools 120 include a single light or a light array 140, one or more visible light projectors 150, a haptic feedback system 160, and an auditory device 170. In some embodiments, generating the local output includes illuminating one or more lights in the light array 140. In some embodiments, illuminating one or more lights in the light array 140 includes illuminating the one or more lights in the light array 140 different colors, different patterns, or of a varying brightness, wherein each of the different colors, patterns, or brightness corresponds to one parameter of the one or more parameters.

In some embodiments, generating the local output configured to be detected by the user using one or more blood vessel correlation tools 120 includes the one or more visible light projectors 150 projecting a blood vessel visualization depiction on the target area 104. In some embodiments, the blood vessel visualization depiction may include different shapes or different colors, wherein each of the different shapes or different colors corresponds to one parameter of the one or more parameters.

In some embodiments, generating the local output configured to be detected by the user using one or more blood vessel correlation tools 120 includes the haptic feedback system 160 vibrating a portion of the ultrasound probe 110 in various patterns, various frequencies, or various magnitudes, wherein each of the various patterns, frequencies, or magnitudes corresponds to one parameter of the one or more parameters. In some embodiments, generating the local output configured to be detected by the user using one or more blood vessel correlation tools 120 includes the auditory device 170 emitting one or more sonic tones having various frequencies, pitches, or patterns, wherein each of the various frequencies, pitches, or patterns correspond to one parameter of the one or more parameters.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical device system configured to detect one or more blood vessels within a target area, comprising:

an ultrasound probe configured to detect the one or more blood vessels, the ultrasound probe in communication with a console; and one or more blood vessel correlation tools of the ultrasound probe, the one or more blood vessel correlation tools configured to generate a local output detectable by a user, the local output corresponding to parameters of the one or more blood vessels, the parameters including:

a blood vessel depth; and one or more of a blood vessel type or a blood vessel size, wherein the one or more blood vessel correlation tools include:

a first visible light projector configured to project a first blood vessel visualization depiction of a first blood vessel on a skin surface within the target area;

a second visible light projector configured to project a second blood vessel visualization depiction of a second blood vessel on the skin surface within the target area, the second blood vessel different from the first blood vessel, wherein the first visible light projector and the second visible light projector are further configured to project first and second visible light projections that include different colors to indicate different parameters of the first blood vessel and the second blood vessel; and one or more of:

a linear light array of individual light-emitting diodes ("LEDs") configured to indicate the parameters of the one or more blood vessels by varying light color, light brightness, or both of the individual LEDs, wherein the local output includes a visible illumination of a single one of the individual LEDs to indicate a lateral location of a detected blood vessel within the target area with respect to the ultrasound probe;

a haptic feedback system configured to indicate the parameters by vibrating a portion of the ultrasound probe; or an auditory device configured to indicate the parameters.

2. The medical device system according to claim 1, wherein the ultrasound probe is configured to detect the one or more blood vessels within the target area using ultrasound waves or near-infrared reflection differentiation by way of a near infrared emitter and detector of the ultrasound probe.

3. The medical device system according to claim 1, wherein the console includes one or more processors, an energy source, a non-transitory computer readable medium, and a plurality of logic modules.

4. The medical device system according to claim 3, wherein the plurality of logic modules, when activated by the one or more processors, are configured to perform operations including:
- receiving detected blood vessel data from the ultrasound probe;
- correlating the detected blood vessel data with the local output corresponding to the parameters of the one or more blood vessels; and
- generating the local output that is detectable by the user.

5. The medical device system according to claim 4, wherein the local output includes:
- a first visible illumination of a first single one of the individual LEDs in the linear light array to indicate a first lateral position of a first detected blood vessel; and
- a second visible illumination of a second single one of the individual LEDs in the linear light array to indicate a second lateral position of a second detected blood vessel,
- wherein the second lateral position is different from the first lateral position.

6. The medical device system according to claim 5, wherein:
- the first visible illumination includes a first brightness indicating a first depth of the first blood vessel,
- the second visible illumination includes a second brightness indicating a second depth of the second blood vessel,
- the second depth is different from the first depth, and
- the second brightness is different from the first brightness.

7. The medical device system according to claim 4, wherein the first and second visible light projections include different brightnesses to indicate the parameters.

8. The medical device system according to claim 7, wherein the first and second visible light projections include lasers.

9. The medical device system according to claim 7, wherein the first and second visible light projections are further configured to project text to indicate the parameters.

10. The medical device system according to claim 4, wherein:
- the one or more blood vessel correlation tools include the auditory device,
- the local output includes an auditory signal from the auditory device, and
- the auditory signal includes different sonic tone frequencies or sonic tone intensities to indicate the parameters.

11. The medical device system according to claim 10, wherein the auditory signal further includes auditory messages to indicate the parameters.

12. The medical device system according to claim 4, wherein:
- the one or more blood vessel correlation tools include the haptic feedback system,
- the local output includes the vibrations of the portion of the ultrasound probe, and
- the vibrations include different vibrational frequencies, different vibrational intensities, or both to indicate the parameters.

13. The medical device system according to claim 1, wherein the linear light array extends across a width of the ultrasound probe.

14. The medical device system according to claim 1, wherein illuminating the single one of the individual LEDs indicates the lateral location of the detected blood vessel located directly below the linear light array.

15. The medical device system according to claim 1, wherein the single one of the individual LEDs is laterally aligned with the detected blood vessel.

16. The medical device system according to claim 1, wherein the first visible light projector and the second visible light projector are disposed adjacent opposite right and left sides of the ultrasound probe.

17. The medical device system according to claim 1, wherein the first visible light projector and the second visible light projector are configured to simultaneously project the first blood vessel visualization depiction and the second blood vessel visualization depiction.

18. A method of detecting one or more blood vessels within a target area and generating a local output detected by a user, comprising:
- detecting the one or more blood vessels within the target area using an ultrasound probe in communication with a console;
- correlating detected blood vessel data with the local output, the local output corresponding to parameters of the one or more blood vessels, the parameters including one or more of a blood vessel type or a blood vessel size; and
- generating the local output configured to be detected by the user using one or more blood vessel correlation tools of the ultrasound probe, the one or more blood vessel correlation tools including:
  - a first visible light projector configured to project a first blood vessel visualization depiction of a first blood vessel on a skin surface within the target area;
  - a second visible light projector configured to project a second blood vessel visualization depiction of a second blood vessel on the skin surface within the target area, the second blood vessel different from the first blood vessel,
    - wherein the first visible light projector and the second visible light projector are further configured to project first and second visible light projections that include different colors to indicate different parameters of the first blood vessel and the second blood vessel; and
  - one or more of:
    - a linear light array of individual light-emitting diodes ("LEDs") configured to indicate the parameters by varying light color, light brightness, or both of the individual LEDs, wherein the local output includes illuminating a single one of the individual LEDs to indicate a lateral location of a detected blood vessel within the target area with respect to the ultrasound probe;
    - a haptic feedback system configured to indicate the parameters by varying vibrational frequency, vibrational intensity, or both of vibrations in at least a portion of the ultrasound probe; or
    - an auditory device configured to indicate the parameters by varying frequency, patterns, or both in an auditory signal of the auditory device.

19. The method according to claim 18, wherein detecting the one or more blood vessels in the target area using the ultrasound probe the one or more blood vessels by ultrasound waves or near-infrared reflection differentiation by way of a near infrared emitter and detector of the ultrasound probe.

20. The method according to claim 19, wherein the parameters further include a blood vessel location a blood vessel depth within the target area.

21. The method according to claim 20, wherein the local output includes illuminating the single one of the individual LEDs with different colors or brightnesses to indicate the parameters.

22. The method according to claim 20, wherein the first and second visible light projections include different brightnesses to indicate different depths of the one or more blood vessels.

23. The method according to claim 20, wherein:

the one or more blood vessel correlation tools includes the haptic feedback system, the local output includes the vibrations of the at least the portion of the ultrasound probe, and the vibrations are configured to indicate the parameters by varying vibrational patterns.

24. The method according to claim 20, wherein:

the one or more blood vessel correlation tools includes the auditory device, the local output includes the auditory signal from the auditory device, and the auditory signal includes messages configured to indicate the parameters.

* * * * *